US006935133B2

(12) United States Patent
Keeter et al.

(10) Patent No.: US 6,935,133 B2
(45) Date of Patent: Aug. 30, 2005

(54) TEMPERATURE CONTROL CASE FOR MEDICINES

(76) Inventors: Estelle Keeter, P.O. Box 1184, Matteson, IL (US) 60443; Marilyn Y. Keeter, P.O. Box 1184, Matteson, IL (US) 60443

( * ) Notice: Subject to any disclaimer, the term of this patent is extended or adjusted under 35 U.S.C. 154(b) by 0 days.

(21) Appl. No.: 10/705,951

(22) Filed: Nov. 13, 2003

(65) Prior Publication Data

US 2004/0093891 A1 May 20, 2004

Related U.S. Application Data

(60) Provisional application No. 60/425,744, filed on Nov. 13, 2002.

(51) Int. Cl.$^7$ ............................. F25D 3/08; B65D 69/00
(52) U.S. Cl. ......................... 62/371; 62/457.2; 62/372; 206/570
(58) Field of Search ................................ 62/457.2, 371, 62/372; 206/542, 570, 571, 828, 543, 363; 383/110; 220/592.2, 592.25

(56) References Cited

U.S. PATENT DOCUMENTS

| 4,429,793 | A | * | 2/1984 | Ehmann .................... 206/570 |
| 4,738,364 | A |   | 4/1988 | Yeager |
| 4,812,054 | A |   | 3/1989 | Kirkendall |
| 5,400,610 | A | * | 3/1995 | Macedo ..................... 62/130 |
| 5,865,032 | A |   | 2/1999 | MacPherson et al. |
| 5,956,968 | A |   | 9/1999 | Grabowski |
| 6,044,650 | A |   | 4/2000 | Cook et al. |
| 6,067,803 | A |   | 5/2000 | Wolsey et al. |
| 6,253,570 | B1 |  | 7/2001 | Lustig |

* cited by examiner

*Primary Examiner*—Chen Wen Jiang
(74) *Attorney, Agent, or Firm*—Richard C. Litman

(57) ABSTRACT

A temperature control medicine carrying case having an insulated housing, a plurality of interior compartments, an interior pouch, a cooling mechanism and a fastening mechanism, e.g., a zipper closure. The interior surface of the insulated housing comprises two separate portions that are separated along a central axis. The interior pouch is located on a first portion of the interior surface of the insulated housing. The interior pouch is adapted to receive the cooling mechanism. At least one of the interior compartments is located on the exterior surface of the interior pouch and is adapted to receive a container of medicine. A plurality of interior compartments is located on the second portion of the interior surface. These compartments are adapted to receive medical devices that are used for administration of the medicine.

11 Claims, 2 Drawing Sheets

TEMPERATURE CONTROL CASE FOR MEDICINES

CROSS-REFERENCE TO RELATED APPLICATION

This application claims the benefit of U.S. Provisional Patent Application Ser. No. 60/425,744, filed Nov. 13, 2002.

BACKGROUND OF THE INVENTION

1. Field of the Invention

The present invention relates generally to portable medicine carrying cases and, more particularly, to insulated, temperature control carrying cases for medicines.

2. Description of Related Art

Many medications that are prescribed to be taken on a daily basis must be maintained at a certain temperature. If the temperature of these medications are not maintained the potency and stability of the medication may be diminished. This may lead to severe health risks. Medications whose temperature must be maintained include insulin, antibiotics in sterile water, allergy serums, vaccines, penicillin, glyceryltrinitrate, benzodiazepines, pseudoephedrine and many others. In particular, insulin, which must be administered daily or several times daily to diabetics, must be maintained at a temperature lower than 86° F. If the temperature of the insulin is in excess of 86° F., use of the insulin becomes unsafe.

Because of the need to have these medicines both readily available and maintained at a certain temperature, many temperature control carrying cases are available. In general the medications have been carried in cooling packages and in conventional coolers. These conventional cooling packages and coolers are bulky and difficult to carry. There are also carrying cases that use active cooling elements, as opposed to the passive cooling elements in conventional cooling packages and coolers. These devices are generally complex and expensive.

Certain examples of temperature control medicine carrying cases that are representative of the related art are disclosed in U.S. Pat. No. 4,738,364 to Yeager, S., U.S. Pat. No. 5,685,032 to MacPherson et al., U.S. Pat. No. 5,956,968 to Grabowski, U.S. Pat. No. 6,044,650 to Cook et al., U.S. Pat. No. 6,067,803 to Wolsey et al. and U.S. Pat. No. 6,253,570 to Lustig. MacPherson et al. discloses a portable thermoelectric cooling medicine kit. The medicine in the kit is cooled by a Peltier heat pump. The kit further includes components that are Velcro-attached to the lining of the kit.

Yeager, S. discloses a portable medicine protector for maintaining the temperature of medicine stored inside of the protector. The protector comprises a hollow walled container that has a cavity formed therein. The container is filled with a freezable liquid. A cavity is-formed inside of the container for receiving medicine. An outer casing is disposed around the container. The outer casing has a layer of pliable foam insulating material.

Cook discloses an insulated storage container for maintaining a constant temperature. The container comprises an enclosure with a lower portion, an upper portion and a side portion positioned between the lower portion and the upper portion. The lower portion includes a first heat sink comprising a thermal energy absorbing substance. A vial holder holds one or more vials of liquid above the heat sink. A temperature indicator inside of the enclosure indicates when the interior of the enclosure is subjected to temperatures below a certain level.

Grabowski discloses a portable cold pack for cold storage and transporting of medicinal vials placed on a holder. The cold pack has a hollow, thin-walled housing and a base having a socket depression therein for receiving the holder. The hollow walls of the housing contain a refreezable liquid for providing cooling energy. In addition, the patent to Wolsey et al. describes a portable, flexible cooling pouch for cooling and storing vials containing medication. The pouch comprises opposed web members made of a water permeable material that are connected together at the edges.

The patent to Lustig discloses a traveling bag for carrying temperature-sensitive medications, such as insulin, that includes a sensor monitoring the interior temperature and an exterior display showing the measured temperature. The bag interior includes a compartment for storing medication, an assembly for securely holding three insulin injection pens, and a compartment for holding a container of freezing material.

U.S. Pat. No. 4,812,054 to Kirkendall, V. S. discloses an insulated beverage box carrier. The carrier is designed for insulating rectangular cardboard wine containers and other beverage containers having spigot dispensers. The carrier has a rectangular body formed by an assembly of panels. The panels have two outer layers of a flat material encasing an inner layer of thermal insulation. The panels are connected to one another by Velcro and zippers.

A problem exists with these carrying cases in that they do not provide the carrier with private security of the medicines while simultaneously maintaining their temperature. The conventional carrying cases are bulky and difficult to carry along with a purse or a brief case. Also, existing carrying cases do not maintain the temperature of the medicine for an entire day without the need of being refrigerated.

Therefore, what is needed is a carrying case that can maintain the temperature of the medicine in the case. What is further needed is a carrying case that provides the user with a certain degree of privacy. What is still further needed is a carrying case that can maintain the temperature of the medicine in the case for an extended period of time without the need for external refrigeration. Finally, what is further needed is a carrying case that can easily fit inside a purse, briefcase or coat for easy transportation and concealment of the case.

None of the above inventions and patents, taken either singly or in combination, is seen to describe the instant invention as claimed.

SUMMARY OF THE INVENTION

The present invention is a temperature control carrying case meeting some or all of the needs mentioned above. The carrying case maintains the temperature of the medicine inside while providing a flexible, portable and concealable case that can be carried in a purse, coat pocket, briefcase, etc. Preferred embodiments of the present invention comprise an insulated housing with a plurality of open ended compartments inside the housing, together with a cooling medium (e.g., refreezable gel pack) and a fastening mechanism for releasably securing the housing in a closed position.

In accordance with one aspect of the present invention, the temperature control carrying case comprises a flexible, insulated housing having an interior and an exterior. The housing is sufficiently flexible so that the present invention may be folded from an open to a closed position. A fastening mechanism is located in the center of the flexible housing. The fastening mechanism releasably secures the present invention in its closed position.

The interior of the housing is divided at its center by a longitudinal axis, creating first and second interior portions. The first interior portion of the housing includes an open-ended pouch adapted for receiving a cooling medium or pack. The first interior portion further includes a plurality of open-ended compartments located on the outer surface of the pouch. These compartments are adapted to receive varying sized containers of medicine. The cooling medium inside the pouch maintains the temperature of the medicine. The second interior portion of the housing includes a plurality of open-ended compartments, on its surface, that are adapted to receive medical instruments such as swabs, syringes and spoons for oral medications.

Accordingly, it is a principal object of the invention to provide a temperature control carrying case that can maintain the temperature of the contents of the case.

It is another object of the invention to provide a temperature control carrying case that can be easily concealed to provide the carrier with a certain degree of privacy.

It is a further object of the invention to provide a temperature control carrying case that can maintain the temperature of the contents of the case for an extended period of time without the need for additional, external refrigeration.

Still another object of the invention is to provide a temperature control carrying case that can easily be carried and concealed inside a purse, briefcase or coat.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
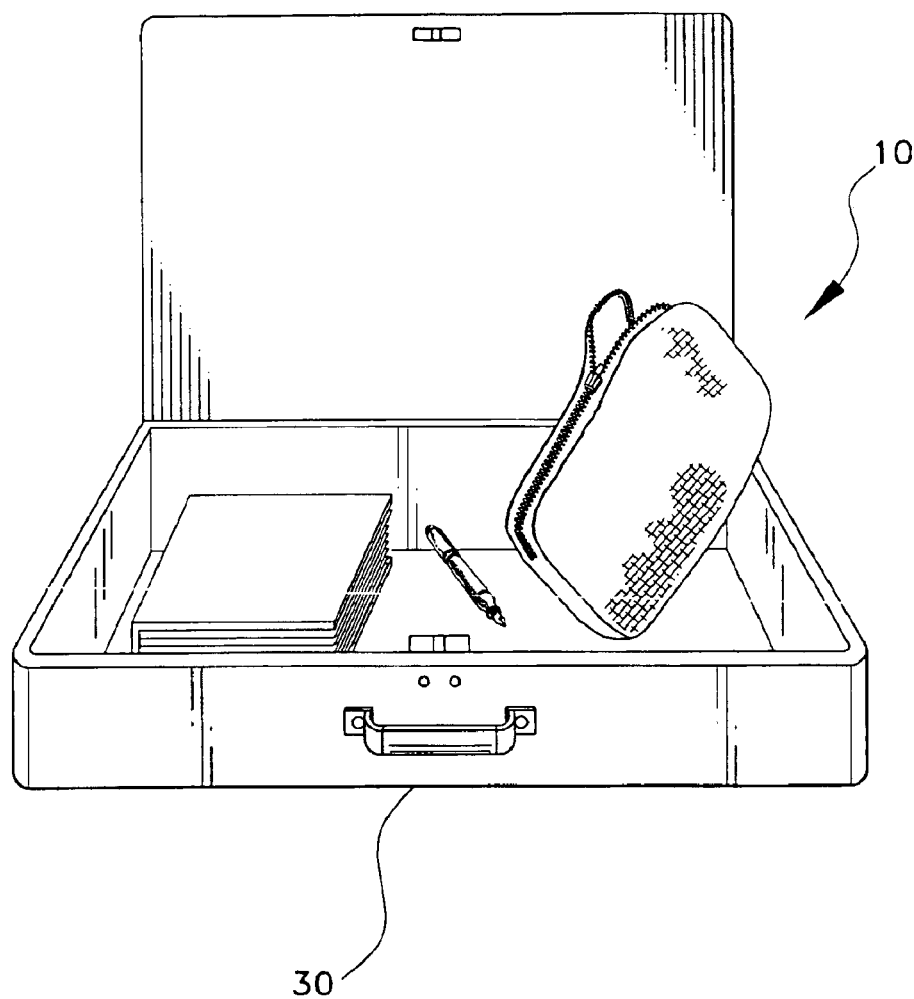
FIG. 1 is an environmental, perspective view of a temperature control case for medicines according to the present invention.

FIG. 1 depicts a temperature control case for medicines according to the present invention. The temperature control case 10 is depicted with reference to a briefcase 30, by way of example. As shown in FIG. 1 the present invention is sufficiently compact to be transported and concealed inside of a briefcase, a purse, a coat pocket, etc. Because the temperature control case 10 is compact it does not require users to carry an additional bag for medications. The compact size of the present invention also provides the user with a greater degree of privacy because the temperature control case 10 may be concealed inside of another bag, or the coat of the user.

Figure 2:
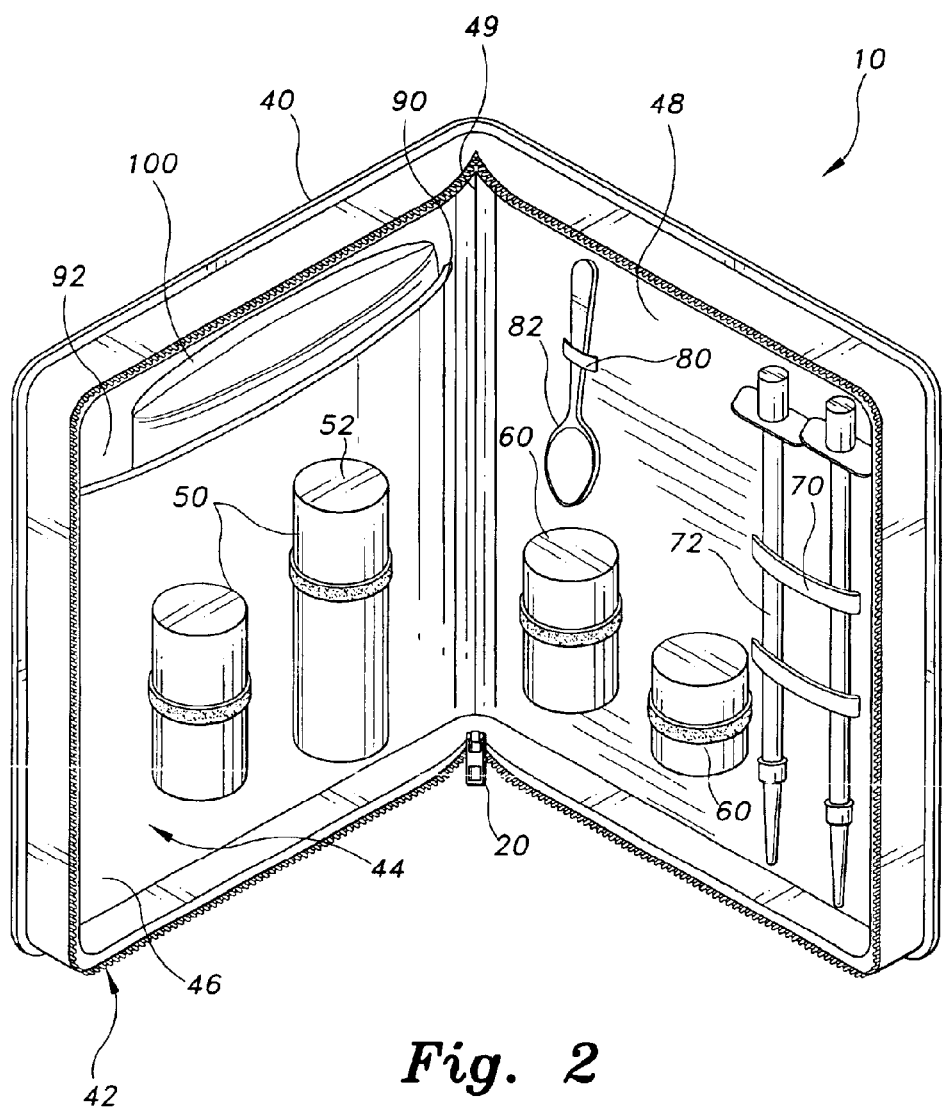
FIG. 2 is an interior view of the temperature control case for medicines depicted in FIG. 1.

FIG. 2 shows the interior view of the temperature control case 10. The temperature control case 10 is depicted as configured for carrying insulin and related accessories used in the administration of insulin. Insulin, which must be administered daily or several times daily to type I diabetics, must be maintained at a temperature lower than 86° F. If the temperature of the insulin is in excess of 86° F., use of the insulin becomes unsafe. Several other medications whose temperature must be maintained include, antibiotics in sterile water, allergy serums, vaccines, penicillin, glyceryltrinitrate, benzodiazepines, and pseudoephedrine, by way of example. If the temperature control case 10 is used for carrying other medications, other accessories necessary for their administration may be incorporated into the temperature control case 10 in a similar manner.

As depicted in FIG. 2 the temperature control case 10 comprises an insulated housing 40, a plurality of interior compartments, a cooling medium 100 and a fastening mechanism 20. Further, the insulated housing 40 has an exterior surface 42 and an interior surface 44. The interior surface 44 is divided in the center along a longitudinal axis 49. The longitudinal axis 49 creates a first interior portion 46 and a second interior portion 48.

The insulated housing 40 should be sufficiently insulated so that the appropriate temperature is maintained inside the temperature control case 10. Also, the insulated housing 40 should be sufficiently insulated so that the appropriate temperature is maintained for a period of 8 to 12 hours. In addition to providing the desired thermal properties, the insulated housing 40 should also be sufficiently flexible in order that the temperature control case 10 may be altered from an open position (depicted in FIG. 2) to a closed position (depicted in FIG. 1).

Preferably, the insulated housing 40 is made of polyethylene with a polyurethane foam under-layer to insure proper insulation. The insulated housing 40 is not limited to being made from these materials and can be made from any suitable material evident to those skilled in the art. The exterior of the temperature control case 10 is made of vinyl.

The fastening mechanism 20 releasably secures the temperature control case 10 in a closed position. When the temperature control case 10 is secured in its closed position it creates a thermally insulated carrying case for medicines that must be maintained at a certain temperature. In the present embodiment depicted in FIG. 2 the fastening mechanism 20 is a zipper. The fastening mechanism 20 is not limited to the zipper depicted in the present embodiment, and can be any mechanism for releasably securing the temperature control case 10 in a closed position.

In order to place the temperature control case 10 in a closed position the first interior portion 46 and the second interior portion 48 are folded along the longitudinal axis 49. Once placed in the closed position the fastening mechanism 20 secures the temperature control case 10 in its closed position.

As shown in FIG. 2, one embodiment of the present invention provides an interior pouch 90 on the first interior portion 46. The interior pouch 90 has one open end 92, which is adapted for receiving the cooling mechanism 100. At least one interior compartment 50 is located on the outer surface of the interior pouch 90. The interior compartments 50 have one open end 52 for receiving containers or medication. The plurality of interior compartments 50 can vary in size to accommodate varying sized containers of medication.

Sleeves 70 and 80 are located on the second interior portion of the insulated housing 40. The sleeves 70 and 80 are adapted for receiving insulin administrating accessories 72 and 82. The accessories depicted in FIG. 2 are a medicine spoon 82 and surgical syringes 72. The plurality of sleeves 70 and 80 may be adapted to receive any other necessary medical accessories. Also located on the second interior surface 48 is a plurality of interior compartments 60. The plurality of interior compartments 60 have open ends 62 for receiving any other appropriate or necessary medical accessories such as swabs or bandages.

Once the temperature controlled case 10 is secured in its closed position the medication will be maintained at its appropriate temperature by the cooling mechanism 100. The cooling mechanism 100 depicted in the present embodiment comprises a refreezable gel pack. In order to maintain the desired temperature control for 8 to 12 hours the preferred embodiment of the present invention use a Lifoam Iceberg Freeze Pack. The cooling pack 100 is not limited to being made from this material and may be ice, or other types of ice packs or gel packs on the market. The Lifoam Iceberg Freeze Pack provides longer temperature control than ordinary ice or gel packs that only maintain the desired temperature for 4–4½ hours.

It is to be understood that the present invention is not limited to the sole embodiment described above, but encompasses any and all embodiments within the scope of the following claims.

We claim:

1. A medicine carrying case comprising:
   a case having a flexible, insulated housing, said housing defining an interior an interior and an exterior surface, said interior surface having a first portion and a second portion, and said housing being foldable along a central axis between an open position and a closed position;
   a cooling mechanism;
   an interior pouch located on said first portion of said interior surface, said interior pouch adapted to receive said cooling mechanism;
   a plurality of interior compartments located on said interior surface of said housing, said plurality of interior compartments include a first set of compartments disposed on the exterior surface of said interior pouch and a second set of compartments disposed on the second portion of said interior surface;
   wherein at least one of said compartments is on an exterior surface of said interior pouch and is adapted to receive a container of medicine;
   a fastening mechanism for releasably securing said housing in said closed position.

2. The medicine carrying case according to claim 1, wherein said insulated housing is made from polyethylene.

3. The medicine carrying case according to claim 1, wherein said insulated housing comprises a polyurethane foam under-layer.

4. The medicine carrying case according to claim 1, wherein said exterior surface of said housing is made from vinyl.

5. The medicine carrying case according to claim 1, wherein said fastening mechanism is a zipper.

6. The medicine carrying case according to claim 1, wherein each of said interior compartments has an open top end adapted for receiving containers of medicine and medicine administering accessories.

7. The medicine carrying case according to claim 6, further comprising a plurality sleeves adapted for receiving medicine accessories.

8. The medicine carrying case according to claim 1, wherein said cooling mechanism is selected from a group consisting of ice, ice packs and refreezable gel packs.

9. The medicine carrying case according to claim 8, wherein said cooling mechanism is a refreezable gel pack.

10. The medicine carrying case according to claim 9, further comprising at least one surgical syringe secured inside of said housing by said plurality of sleeves.

11. The medicine carrying case according to claim 9, further comprising at least one medicinal spoon secured inside of said housing by said plurality of sleeves.

\* \* \* \* \*